United States Patent [19]

Hosoda et al.

[11] 4,146,536

[45] Mar. 27, 1979

[54] NOCARDICIN E AND F, AND PROCESS FOR PRODUCTION THEREOF

[75] Inventors: Junji Hosoda, Kobe; Hatsuo Aoki, Ikeda; Hiroshi Imanaka, Osaka, all of Japan

[73] Assignee: Fujisawa Pharmaceutical Co., Ltd., Osaka, Japan

[21] Appl. No.: 738,144

[22] Filed: Nov. 2, 1976

[30] Foreign Application Priority Data

Nov. 14, 1975 [JP] Japan ................................ 51-137391

[51] Int. Cl.² ..................... A01N 9/22; A61K 31/395; C07D 205/08; C12D 9/22
[52] U.S. Cl. ................................ 260/239 A; 195/109; 195/113; 424/244
[58] Field of Search .................... 260/239 A; 424/118

[56] References Cited

U.S. PATENT DOCUMENTS 3,923,977  12/1975  Aoki et al. ........................... 424/118

FOREIGN PATENT DOCUMENTS 2529941  8/1976  Fed. Rep. of Germany ...... 260/239 A

OTHER PUBLICATIONS

Hashimoto et al., J. Am. Chem. Soc., vol. 98, pp. 3023–3025 (1976).

*Primary Examiner*—Alton D. Rollins
*Attorney, Agent, or Firm*—Dayton R. Stemple, Jr.

[57] ABSTRACT

This invention relates to new compounds having antibacterial activity.

More particularly, it relates to new antibiotics, Nocardicin E and F and to a process for production of the same by fermentation.

3 Claims, No Drawings

NOCARDICIN E AND F, AND PROCESS FOR PRODUCTION THEREOF

BRIEF SUMMARY OF THE INVENTION

Accordingly, it is an object of this invention to provide new antibiotics, Nocardicin E and F having antibacterial activities against a pathogenic bacteria, especially *Pseudomonas aeruginosa*.

Another object of this invention is to provide a process for the production of the antibiotic Nocardicin E and F by fermentation of a Nocardicin E and/or F producing strain belonging to the genus Nocardia in a nutrient medium.

The object compounds of this invention, Nocardicin E and F (hereinafter referred to as the present Nocardicins) are represented by the following formulae.

Nocardicin E

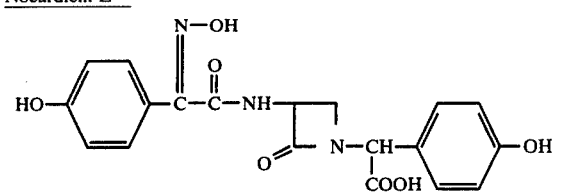

Nocardicin F

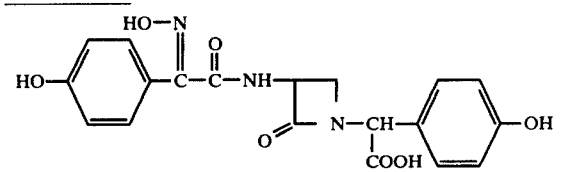

Microorganism to be used in this invention is a strain belonging to the genus Nocardia which is capable of producing Nocardicin E and/or F.

Among such an organism, preferred one is *Nocardia uniformis* subsp. *tsuyamanensis*, a strain of which was deposited on June 13, 1972 with American Type Culture Collection (ATCC) located in 12301 Parklawn Drive Rockville, Maryland 20852, USA and assigned the ATCC number 21806. This deposited *Nocardia uniformis* subsp. *tsuyamanensis* ATCC 21806 is now available to the public and the details thereof, i.e. the microbiological characteristics, etc. are disclosed in literatures, e.g. U.S. Pat. No. 3,923,977 and German Offenlegungsschrift No. 2242699.

It is to be understood that, for the production of the present Nocardicins, this invention is not limited to the use of (specific) organism described herein, which is given only for illustrative purpose. Further, this invention also includes the use of natural mutants as well as artificial ones which can be derived from the microorganism as described herein in a conventional manner such as radiation with X-rays or ultraviolet, treatment with N-methyl-N'-nitro-N-nitrosoguanidine, 2-aminopurine or nitrogen mustards, and the like.

The present Nocardicins are produced by culturing a Nocardicin E and/or F - producing strain belonging to the genus Nocardia such as *Nocardia uniformis* subsp. *tsuyamanensis* in a nutrient medium containing assimilable carbon and nitrogen sources under submerged aerobic conditions. Further, as a nutrient of the medium, there may be used any nutrient which can be utilized by the said microorganism for production of the present Nocardicins.

The preferred sources of carbon are carbohydrates such as glucose, sucrose, maltose, glycerin, starch and the like. The preferred sources of nitrogen are organic nitrogen sources such as yeast extracts, peptone, gluten meal, cottonseed meal, soybean meal, corn meal, dried yeast, beef extracts, casein hydrolysate, corn steep liquor, urea and the like, and inorganic nitrogen sources such as ammonium salts (e.g. ammonium nitrate, ammonium sulfate, ammonium phosphate, etc.) and the like.

If desired, there may be added to the medium, mineral salts such as calcium carbonate, sodium or potassium phosphate, magnesium chloride or sulfate and the like as a minor component. Further, there may be added to the medium, one or more organic compounds such as tyrosine, glycine, serine, homoserine, p-hydroxyphenylglycine, α-aminobutyric acid, α,β-diaminopropionic acid, N-acetyltyrosine, N-acetyltyrosinamide, p-hydroxy phenylpyruvic acid, p-hydroxyphenylglycolic acid, p-hydroxyphenylglyoxalic acid, shikimic acid, 2-amino-3-(4-hydroxyphenyl)propionohydroxamic acid, 2-acetamido-3-(4-hydroxyphenyl)propionohydrazide and the like. These organic compounds may work as a kind of precusor and may be useful for elevating the productivity of the present Nocardicins.

In the fermentation process, submerged aerobic cultural conditions are preferably employed for the production of the present Nocardicins in massive amount. It is to be understood also that for the production in limited amounts, a shaking or surface culture in a flask or bottle can be employed. Furthermore, when the growth is carried out in large tanks, it is preferable to use the vegetative form of the organism for inoculation in the production tanks in order to avoid growth lag in the process of production of the present Nocardicins. Accordingly, it is desirable first to produce a vegetative inoculum of the organism by inoculating a relatively small quantity of culture medium with spores or mycelia of the organism and culturing them, and to transfer the cultured vegetative inoculum aseptically to large tanks. The medium in which the vegetative inoculum is produced can be the substantially same as or different from medium utilized for the production of the present Nocardicins.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture. In the course of fermentation, especially when the culture medium is foamed remarkably, a defoaming agent such as plant oils (e.g., soybean oil, etc.), higher alcohols (e.g. octadecanol, tetradecanol, etc.), silicones and the like, may be added to the medium.

The fermentation is usually conducted at a temperature about between 20° C. and 40° C., preferably about 30° C., for a period of 50 hours to 100 hours.

DETAILED DESCRIPTION

The present Nocardicins, as produced above, can be recovered from the cultured broth in a conventional manner, which are generally used for the recovery of fermentation products. The present Nocardicins in the cultured broth are present in mycelia (intracellularly) and/or out of mycelia (extracellularly).

As the first step, the cultured broth is divided into filtrate (supernatant) and filter cake by means of filtration or centrifuge.

Extraction of the present Nocardicins from the filter cake is conducted by treating said cake with an organic solvent in which the present Nocardicins can be soluble, for example, alcohols (e.g. methanol, ethanol, etc.), ketones (e.g. acetone etc.), aqueous alcohols (e.g. aqueous methanol, aqueous ethanol, etc.) and the like.

From thus obtained filtrate and/or extract, the present Nocardicins may be isolated and purified by conventional means.

As said conventional means, there may be exemplified, treatment with adsorbents (e.g. activated charcoal, silicic acid, silica gel, alumina, etc.), anionic or cationic exchange resins, or macroporous nonionic adsorption resins [e.g. Amberlite XAD-2, XAD-4, XAD-7 and XAD-8 (trade name, made by Rohm & Haas Co.), Diaion HP10, HP20, HP30, HP40 and HP50 (trade name, made by Mitsubishi Chemical Industries Ltd.), etc.]; extraction with solvent; concentration under reduced pressure; lyophilization; pH adjustment; crystallization; recrystallization; and the like. These means may be preferably employed independently or in combination thereof in optional order or repeatedly.

Nocardicin E and/or Nocardicin F can be separated and isolated by treating a crude material comprising the same with adsorbent which is capable of selectively adsorbing the same. As the preferred adsorbent, there are exemplified silicic acid, etc. And, as the crude material comprising Nocardicin E and/or F, there can be used a filtrate obtained by filtrating the culture broth or the partially purified material thereof (e.g. extracts, eluates, etc.), and the like. For example, Nocardicin E and/or F are isolated by subjecting the crude material to a column chromatography on silicic acid with a suitable developing solvent [e.g. a mixture of chloroform and ethyl acetate (4:1), a mixture of chloroform and methanol (10:1)], and fractions containing Nocardicin E and/or F are collected, respectively.

Each of Nocardicin E and F can be purified from each of the fractions as obtained in the above in a conventional manner.

The present Nocardicins, produced in the culture broth, can be isolated in the free form, and optionally in the form of their alkali metal salts by treating crude material containing the present Nocardicins with an alkali metal material (e.g. sodium or potassium hydroxide) during the isolation or purification processes.

The present Nocardicins obtained in their free form may be also converted to the salt with an inorganic or organic base (e.g. potassium or sodium hydroxide, ethanolamine, dicyclohexylamine, etc.) in a conventional manner.

Further, the inorganic or organic base salt of the present Nocardicins may be easily converted to their free form by treating the said salt with an acid such as a mineral acid (e.g. hydrochloric acid, etc.) in a conventional manner.

Table 1.

| | Physicochemical Properties of Nocardicin E and F | |
|---|---|---|
| | Nocardicin E | Nocardicin F |
| Appearance | White crystals<br>Weakly acidic | White crystals<br>Weakly acidic |
| Elemental analysis [%] | C56.95:H4.20:N10.48 | C56.84:H4.35:N10.23 |
| Optical rotation | $[\alpha]_D^{24} = 192°$ (C = 1, H$_2$O) | $[\alpha]_D^{24} = -181°$ (C = 1, H$_2$O) |
| Melting point | 228–231° C (decomp.) | 230–231° C (decomp.) |
| UV spectrum | $\lambda\max(E^{1\%}_{1cm}) = 222$(sh, 557), 272(396)nm in CH$_3$OH 248(719), 298(324)nm in CH$_3$OH-1N aq. NaOH (9:1) | $\lambda\max(E^{1\%}_{1cm}) = 224$(516), 270(248)nm in CH$_3$OH, 247(720), 295(253)nm in CH$_3$OH-1N aq. NaOH (9:1) |
| IR spectrum | $\nu_{max}^{nujol}$ = 3380,3280,2920, 2840,1745,1675,1645 1610,1595,1540,1515, 1510,1460,1435,1375 1360,1325,1310,1275, 1260,1220,1175,1140, 1115,1105,1055,1030, 1005,945,935,910,855, 845,825,755,730, 700,685cm$^{-1}$ | $\nu_{max}^{nujol}$ = 3420,3300,3280, 2950,2920,1900,1745, 1680,1655,1610,1595, 1550,1515,1465,1450, 1410,1380,1360,1310, 1295,1280,1270,1250, 1220,1180,1140,1120, 1110,1060,1030,1010, 980,935,900,870,860, 840,820,780,740,720, 680cm$^{-1}$ |
| Color reaction | Positive: ferric chloride-potassium ferricyanide reaction<br>Negative: Ehrlich test, ninhydrin reaction | Positive: ferric chloride-potassium ferricyanide reaction<br>Negative: Ehrlich test, ninhydrin reaction |
| Solubility | Highly soluble: aqueous alkaline solution (e.g. aqueous ammonia, aqueous sodium hydroxide solution), pyridine, dimethylsulfoxide,<br>Sparingly soluble:CH$_3$OH, C$_2$H$_5$OH,<br>Insoluble: CH$_3$COCH$_3$ CH$_3$COOC$_2$H$_5$, CHCl$_3$ | Highly soluble: aqueous alkaline solution, pyridine, dimethylsulfoxide<br>Sparing soluble:CH$_3$OH, C$_2$H$_5$OH<br>Insoluble: CH$_3$COCH$_3$ CH$_3$COOC$_2$H$_5$, CHCl$_3$ |

TABLE 2.

| Thin Layer Chromatography of Nocardicins E and F | | |
|---|---|---|
| Carrier | : Eastman Chromagram Sheet Cellulose No. 6065 (containing fluorscent agent) (trade name, Eastman Kodak Co.) | |
| Detection | : UV absorption method | |
| | Rf Value | |
| Developing Solvent | Nocardicin E | Nocardicin F |
| n-butanol-acetic acid-water (4:1:2) | 0.84 | 0.89 |

TABLE 2.-continued

Thin Layer Chromatography of Nocardicins E and F

| Carrier | : Eastman Chromagram Sheet Cellulose No. 6065 (containing fluorscent agent) (trade name, Eastman Kodak Co.) |
|---|---|
| Detection | : UV absorption method |

| | Rf Value | |
|---|---|---|
| Developing Solvent | Nocardicin E | Nocardicin F |
| n-butanol saturated with water | 0.29 | 0.41 |
| n-propanol-water (7:3) | 0.67 | 0.74 |

TABLE 3.

NMR Spectrum of Nocardicin E and F

| Nocardicin | E | F |
|---|---|---|
| Solvent | DMSO-$d_6$ | DMSO-$d_6$ |
| Internal Standard | TMS | TMS |
| δppm | 3.12 (1H,m) | 3.14 (1H,m) |
| | 3.79 (1H,t,J = 5Hz) | 3.74 (1H,t,J = 5Hz) |
| | 4.98 (1H,m) | 4.94 (1H,m) |
| | 5.33 (1H,s) | 5.31 (1H,s) |
| | 6.78 (4H,d,J = 8Hz) | 6.78 (4H,d,J = 8Hz) |
| | 7.16 (2H,d,J = 8Hz) | 7.17 (2H,d,J = 8Hz) |
| | 7.30 (2H,d,J = 8Hz) | 7.39 (2H,d,J = 8Hz) |
| | 9.06 (1H,d,J = 8Hz) | 8.82 (1H,d,J = 8Hz) |
| | 9.70 (3H, broad s) | 11.60 (1H, broad s) |
| | 11.14 (1H,s) | |

As the result of further study, chemical structures of the present Nocardicins having the above physico-chemical properties have been identified and assigned as mentioned above.

The present Nocardicins and their salts possess specific antibiotic spectrums, showing activity against pathogenic bacteria with low toxicity. Accordingly, the present Nocardicins and salts thereof may be useful in treatment of infectious diseases caused by such bacteria in mammals.

The pharmacological tests of the present Nocardicins i.e. antimicrobial and toxicity tests are mentioned as follows.

Minimum Inhibitory Concentration (M.I.C.)

M.I.C. test was conducted by a usual serial agar dilution method, using Mueller Hinton agar (Inoculum: $10^6$ cells/ml) which was incubated at 37° C. for 20 hours. M.I.C. value is expressed as the minimum concentration of the Nocardicin E or F (mcg/ml) which inhibits growth of the microorganism. The results are shown in the following table 4.

TABLE 4.

Minimum Inhibitory Concentration

| | M.I.C. (mcg/ml) | |
|---|---|---|
| Test Microorganism | Nocardicin E | Nocardicin F |
| Staphylococcus aureus 209P | >400 | >400 |
| Bacillus subtilis ATCC6633 | >400 | >400 |
| Escherichia coli NIHJ JC-2 | >400 | >400 |
| Pseudomonas aeruginosa NCTC10490 | 12.5 | 100 |

Acute Toxicity

Each of aqueous sodium hydroxide solution (pH 7.4) of Nocardicin E or F was subcutaneously injected in each of five ICR-strain mice weighing 18-22g (Dose: 500mg/kg) and the observation was continued for one week after said administration, as the results of which all the mice tested were normal for said period.

The present Nocardicins and pharmaceutically acceptable salt thereof can be formulated for administration in any convenient way, analogously with known antibiotics, by admixture with a pharmaceutical carrier.

A pharmaceutically acceptable salt of the present Nocardicins may include salt with an inorganic or organic base such as sodium hydroxide, potassium hydroxide, calcium hydroxide, ammonia, ethanolamine, triethylamine, dicyclohexylamine and the like.

Thus, the antimicrobial composition can be used in the form of pharmaceutical preparation, for example, in solid, semisolid or liquid form, which contains the active object compound in admixture with a pharmaceutical organic or inorganic carrier or excipient suitable for external, enteral or parenteral applications. The active ingredient may be compounded, for example, with usual carriers for tablets, peletts, capsules, suppositories, solutions, emulsions, suspensions, and other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes. The antimicrobial compositions can also contain preserving or bacteriostatic agents thereby keeping the active ingredient in the desired preparations stable in activity. The present Nocardicins or salts thereof is included in the antimicrobial composition in an amount sufficient to produce the desired therapeutic effect upon the bacterially infected process or condition.

The present Nocardicins can be also used as intermediates for preparing the other 3-acylamino-1-(α-carboxy-4-hydroxybenzyl)-2-azetidinone, which is more improved in the antimicrobial activity against pathogenic Gram-positive bacteria.

The following examples are given for the purpose of illustrating this invention.

EXAMPLE 1 (Production of Nocardicin E)

An aqueous medium (300 ml.) containing 2% of sucrose, 2% cottonseed meal, 1% of dried yeast, 2.18% of $KH_2PO_4$ and 1.43% of $Na_2HPO_4.12H_2O$ was poured into one liter Erlenmeyer flask and sterilized at 120° C. for 20 minutes. A loopful of slant culture of *Nocardia uniformis* subsp. *tsuyamanensis* ATCC 21806 was inoculated into the medium and cultured at 30° C. for 54 hours.

Into a 500-liter fermenter, there was placed the same medium (150 liters) as mentioned above. The fermentation medium was sterilized at 120° C. for 20 minutes and then inoculated with the whole volume of the vegetative inoculum prepared above, and cultured at 30° C. for 42 hours.

On the other hand, an aqueous medium (3000 liters) containing 2% of soluble starch, 1% of peptone, 0.4% of yeast extracts, 1% of $KH_2PO_4$, 1% of $Na_2HPO_4.12H_2O$, 0.5% of $MgSO_4.7H_2O$, 0.1% of L-tyrosine and 0.1% of glycine was poured into 4000-liter fermenter and sterilized at 120° C. for 20 minutes. The whole volume of the cultured broth, as prepared above, was inoculated into the medium.

The organism was grown in the fermentation medium at 30° C., for 119 hours. During the growth period, the broth was stirred at 230 r.p.m. and sterile air was passed through the broth in a ratio of 3000 liters per minute. After the culture was completed, the cultured broth was filtered with the aid of diatomaceous earth (180 Kg.). To a part of the filtrate (1500 liters), there was added activated charcoal (45 Kg.), whereafter the mixture was stirred for 30 minutes and filtered to separate the activated charcoal. To the activated charcoal was added a mixture of acetone and water (7:3) (200 liters), whereafter the resultant mixture was adjusted to pH 8.0 with an aqueous ammonia and stirred for 60 minutes. The eluate (500 liters) thus obtained was concentrated to a volume of 50 liters. The concentrate was adjusted to pH 4.0 with 6N hydrochloric acid. subsequently, to the concentrate, there was added n-butanol (60 liters), whereafter the mixture was stirred for 30 minutes. The n-butanol layer (50 liters) was separated and concentrated under reduced pressure to a volume of 10 liters. The concentrate was adjusted to pH 8.0 with 5% aqueous ammonia and stirred for 30 minutes. The aqueous layer (15 liters) was separated and concentrated under reduced pressure to a volume of 1.3 liters. The concentrate was adjusted to pH 4.0 with 6N hydrochloric acid, mixed with diatomaceous earth (1.3 Kg.) and then dried. The powder was washed with chloroform (3 liters) and the object compound was eluted with ethyl acetate. The eluate (5 liters) was concentrated under reduced pressure to a volume of 50 ml. The concentrate was mixed with diatomaceous earth (50g.) and dried. The powder was subjected to a column chromatography on silicic acid (developing solvent : ethyl acetate). The eluate (600 ml.) was concentrated under reduced pressure to a volume of 10 ml. The concentrate was mixed with diatomaceous earth (10 g.) and dried. The powder was subjected to a column chromatography on silicic acid [developing solvent : a mixture of chloroform : methanol (100:7)]. The eluate (200 ml.) was concentrated under reduced pressure to a volume of 3 ml. Subsequently, the concentrate was mixed with diatomaceous earth (3 g.) and dried. The powder was subjected to a column chromatography on silicic acid [developing solvent : a mixture of chloroform : ethyl acetate (1:4)]. The eluate (50 ml.) was evaporated to dryness under reduced pressure. The residue thus obtained was dissolved in methanol (1 ml.). To the solution, there was added chloroform (5 ml.) and allowed to stand overnight at 4° C. to give crystals (230 mg.), which were recrystallized from a mixture of methanol and chloroform (1:5) (12 ml.) to give Nocardicin E (190 mg.) in the form of white crystals.

EXAMPLE 2 (Production of Nocardicin F)

An aqueous medium (100 ml.) containing 2% of sucrose, 2% of cottonseed meal, 1% of dried yeast, 2.18% of $KH_2PO_4$, 1.43% of $Na_2HPO_4.12H_2O$ was poured into each of twenty four 500-ml. Sakaguchi flasks and sterilized at 120° C. for 20 minutes. A loopful of slant culture of Nocardia uniformis subsp. *tsuyamanensis* ATCC 21806 and the organism was cultured at 30° C. for 48 hours.

On the other hand, an aqueous medium (20 liters) containing 2% of soluble starch, 1% of peptone, 0.4% of yeast extracts, 1% of $KH_2PO_4$, 1% of $Na_2HPO_4.12H_2O$, 0.5% of $MgSO_4.7H_2O$, 0.1% of L-tyrosine and 0.1% of glycine was poured into each of six 30-liter jar fermenter and sterilized at 120° C. for 20 minutes. Subsequently, the cultured broth, as obtained above, was inoculated into each of the media in a ratio of 2% by volume of the medium. The organism was grown in the medium at 30° C. for 96 hours. During the growth period, the broth was stirred at 250 r.p.m. and sterile air was passed through the broth in a ratio of 20 liters per minutes. After the culture was completed, the cultured broth (100 liters) was filtered with the aid of diatomaceous earth (10 Kg.). To the filtrate (90 liters), there was added an activated charcoal (1.5 Kg.), whereafter the mixture was stirred for 10 minutes and then filtered. The activated charcoal was washed twice with water (10 liters) and the object compound was eluted twice with 80% aqueous methanol (30 liters and 20 liters). The eluate (50 liters) was concentrated under reduced pressure to a volume of 6 liters. The concentrate was adjusted to pH 4.0 with 6N hydrochloric acid and passed through a column packed with Diaion HP 20 (3 liters). After the column was washed with water (1 liter), the object compound was eluted with 40% ethanol (8 liters). The fractions (4 liters) containing the object compound was collected and concentrated under reduced pressure to a volume of 100 ml. The concentrate was mixed with powdery cellulose (300 g.), whereafter the mixture was dried under reduced pressure. The dried powder was packed into a column and elution was carried out with acetone (6 liters) from the column. The eluate was concentrated under reduced pressure to a volume of 50 ml. The concentrate was mixed with diatomaceous earth (50 g.) and the mixture was dried. The dried mixture was subjected to a column packed with silicic acid [developing solvent : a mixture of chloroform and methanol (10:1)]. The fractions containing the object compound were collected and evaporated to dryness under reduced pressure. The residue thus obtained was dissolved in methanol (20 ml.). To the solution, there was added water (40 ml.), whereafter the mixture was allowed to stand overnight at 4° C. to give precipitates (560 mg.), which were separated by filtration and dissolved in methanol (10 ml.). To the solution, there was added water (20 ml.), whereafter the mixture was allowed to stand overnight at 4° C. to give crystals, which were separated and dried to give Nocardicin F (300 mg.) in the form of white crystals.

We claim:

1. A Nocardicin compound substantially free of other Nocardicins, having a white crystalline form and having the following formula:

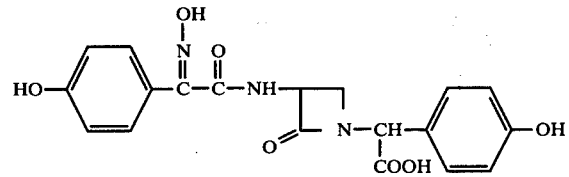

2. A compound of claim 1 known as Nocardicin E and having the following formula

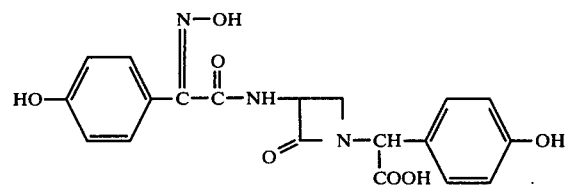

3. A compound of claim 1 known as Nocardicin F and having the following formula

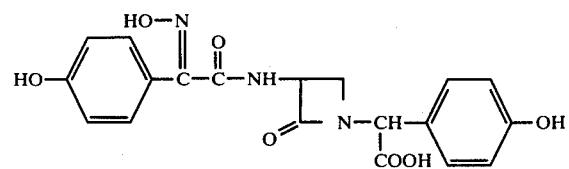

* * * * *